United States Patent
Miesel et al.

(10) Patent No.: US 9,381,039 B2
(45) Date of Patent: Jul. 5, 2016

(54) FILLING METHODS AND APPARATUS FOR IMPLANTED MEDICAL THERAPY DELIVERY DEVICES

(71) Applicant: Medtronic, Inc., Minneapolis, MN (US)

(72) Inventors: Keith A. Miesel, St. Paul, MN (US); Scott A. Sarkinen, Greenfield, MN (US); Emem D. Akpan, Coon Rapids, MN (US); Douglas E. Hentges, Andover, MN (US); Mark E. Dunlap, St. Francis, MN (US); Darrin Schauble, Phoenix, AZ (US); Cindy Konen, Minneapolis, MN (US); Mark R. Bilitz, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 551 days.

(21) Appl. No.: 13/840,718

(22) Filed: Mar. 15, 2013

(65) Prior Publication Data
US 2014/0276573 A1    Sep. 18, 2014

Related U.S. Application Data

(63) Continuation-in-part of application No. 13/426,045, filed on Mar. 21, 2012, now abandoned.

(51) Int. Cl.
*A61B 17/34* (2006.01)
*A61M 39/02* (2006.01)

(52) U.S. Cl.
CPC ........ *A61B 17/3417* (2013.01); *A61M 39/0208* (2013.01); *A61M 2039/0244* (2013.01)

(58) Field of Classification Search
CPC .......... A61B 17/3417; A61M 39/0208; A61M 2039/0244

USPC .......... 604/22, 65–67, 131, 93.01, 604/288.01–288.04
See application file for complete search history.

(56) References Cited

U.S. PATENT DOCUMENTS

| 4,573,994 A | 3/1986 | Fischell et al. |
| 4,804,054 A | 2/1989 | Howson et al. |

(Continued)

FOREIGN PATENT DOCUMENTS

| WO | WO2007/107561 | 9/2007 |
| WO | WO2009/029044 | 3/2009 |

(Continued)

OTHER PUBLICATIONS

PCT/US2013/033060 Search Report and Written Opinion dated Jul. 30, 2013.

*Primary Examiner* — Manuel Mendez

(57) ABSTRACT

Transdermal insertion of a transcutaneous filling apparatus, for the purpose of filling a fill chamber of an implanted therapy delivery device, is monitored by measuring each impedance between pairs of electrodes of a needle of the apparatus, and comparing each to a threshold impedance; the electrodes, preferably at least three in number, are isolated and spaced apart from one another along a length of the needle. A confirmation signal is generated when at least one of the measured impedances is greater than the threshold impedance, and another is less than the threshold, the condition indicating that one of the electrodes is located within a non-conductive septum, through which the apparatus must pass to access the fill chamber. A detection circuit, which may be located in a housing of the apparatus that is attached to a proximal end of the needle, measures and compares the impedances.

24 Claims, 11 Drawing Sheets

(56) References Cited

U.S. PATENT DOCUMENTS

| | | | |
|---|---|---|---|
| 5,009,644 A | 4/1991 | McDonald | |
| 5,078,714 A * | 1/1992 | Katims | 606/38 |
| 5,171,228 A | 12/1992 | McDonald | |
| 5,536,240 A * | 7/1996 | Edwards et al. | 604/22 |
| 5,730,719 A * | 3/1998 | Edwards | 604/22 |
| 5,800,379 A * | 9/1998 | Edwards | 604/22 |
| 5,843,026 A * | 12/1998 | Edwards et al. | 604/508 |
| 5,921,933 A | 7/1999 | Sarkis et al. | |
| 5,921,954 A * | 7/1999 | Mohr et al. | 604/508 |
| 6,048,328 A | 4/2000 | Haller et al. | |
| 6,203,523 B1 | 3/2001 | Haller et al. | |
| 6,306,094 B1 | 10/2001 | Joseph | |
| 6,308,097 B1 * | 10/2001 | Pearlman | 600/547 |
| 6,356,783 B1 | 3/2002 | Hubbard, Jr. | |
| 6,610,016 B1 | 8/2003 | Violante et al. | |
| 6,709,380 B2 | 3/2004 | Green et al. | |
| 6,740,076 B2 | 5/2004 | Hoben et al. | |
| 6,962,580 B2 | 11/2005 | Adams et al. | |
| 7,106,574 B2 | 9/2006 | Beyerlein | |
| 7,470,249 B2 | 12/2008 | Junger | |
| 7,580,743 B2 | 8/2009 | Bourlion et al. | |
| 7,637,897 B2 | 12/2009 | Ginggen | |
| 7,749,528 B2 | 7/2010 | De Carvalho et al. | |
| 7,780,631 B2 | 8/2010 | Lum et al. | |
| 7,806,122 B2 | 10/2010 | Hoendervoogt et al. | |
| 7,942,863 B2 | 5/2011 | Kalpin et al. | |
| 7,987,001 B2 | 7/2011 | Teichman et al. | |
| 2006/0089619 A1 | 4/2006 | Ginggen | |
| 2009/0036794 A1 | 2/2009 | Stubhaug et al. | |
| 2009/0082757 A1 | 3/2009 | Rogers et al. | |
| 2009/0234302 A1 | 9/2009 | Hoendervoogt et al. | |
| 2010/0125246 A1 | 5/2010 | Kalpin | |
| 2010/0168684 A1 | 7/2010 | Ryan | |
| 2010/0286507 A1 | 11/2010 | Paassilta et al. | |
| 2011/0238034 A1 | 9/2011 | Kalpin | |
| 2012/0289819 A1 | 11/2012 | Snow | |

FOREIGN PATENT DOCUMENTS

| | | |
|---|---|---|
| WO | WO2010/051262 | 5/2010 |
| WO | WO2010/075292 | 7/2010 |

* cited by examiner

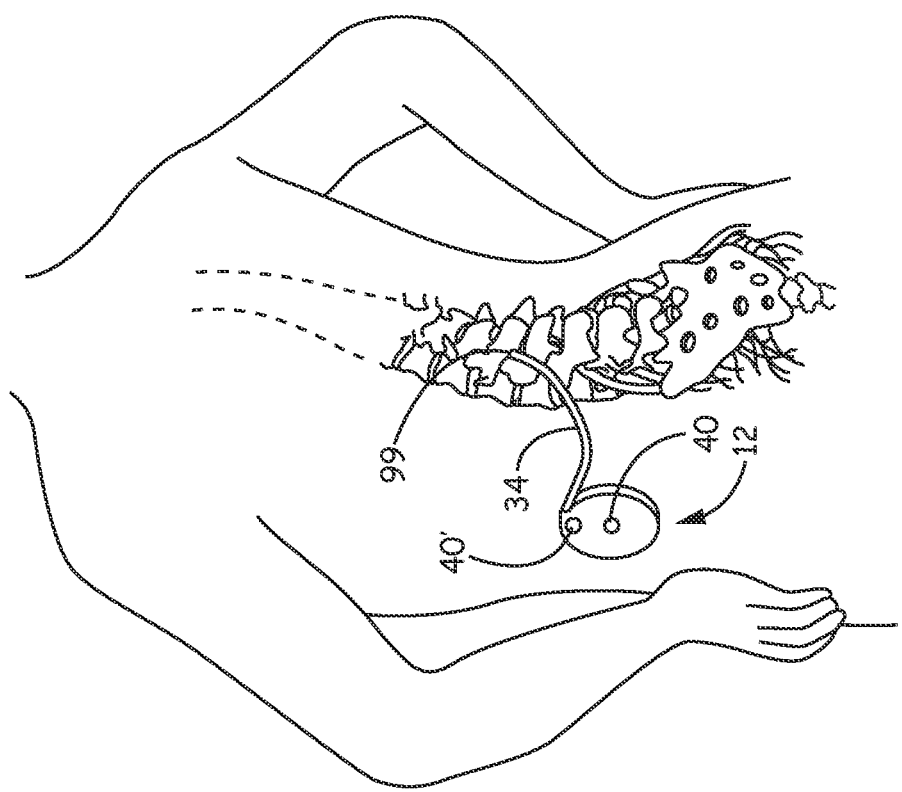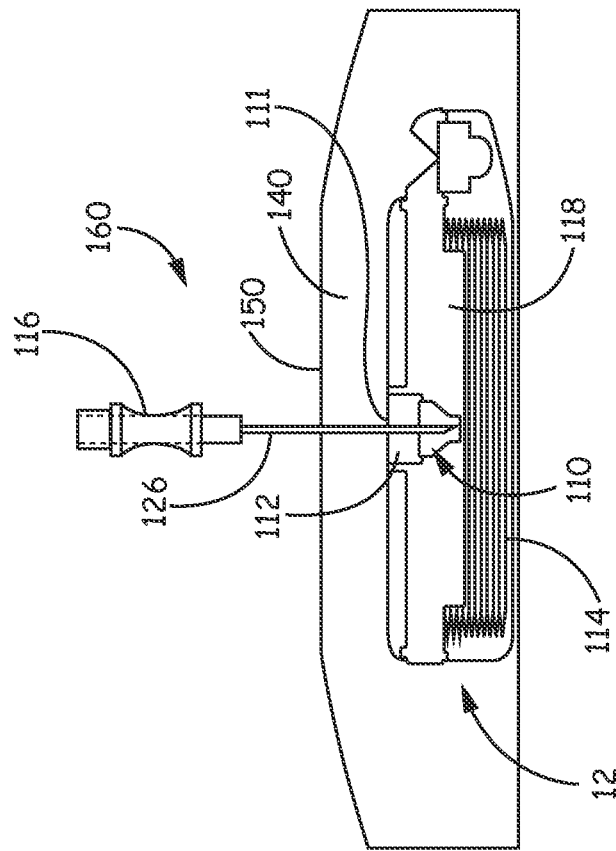

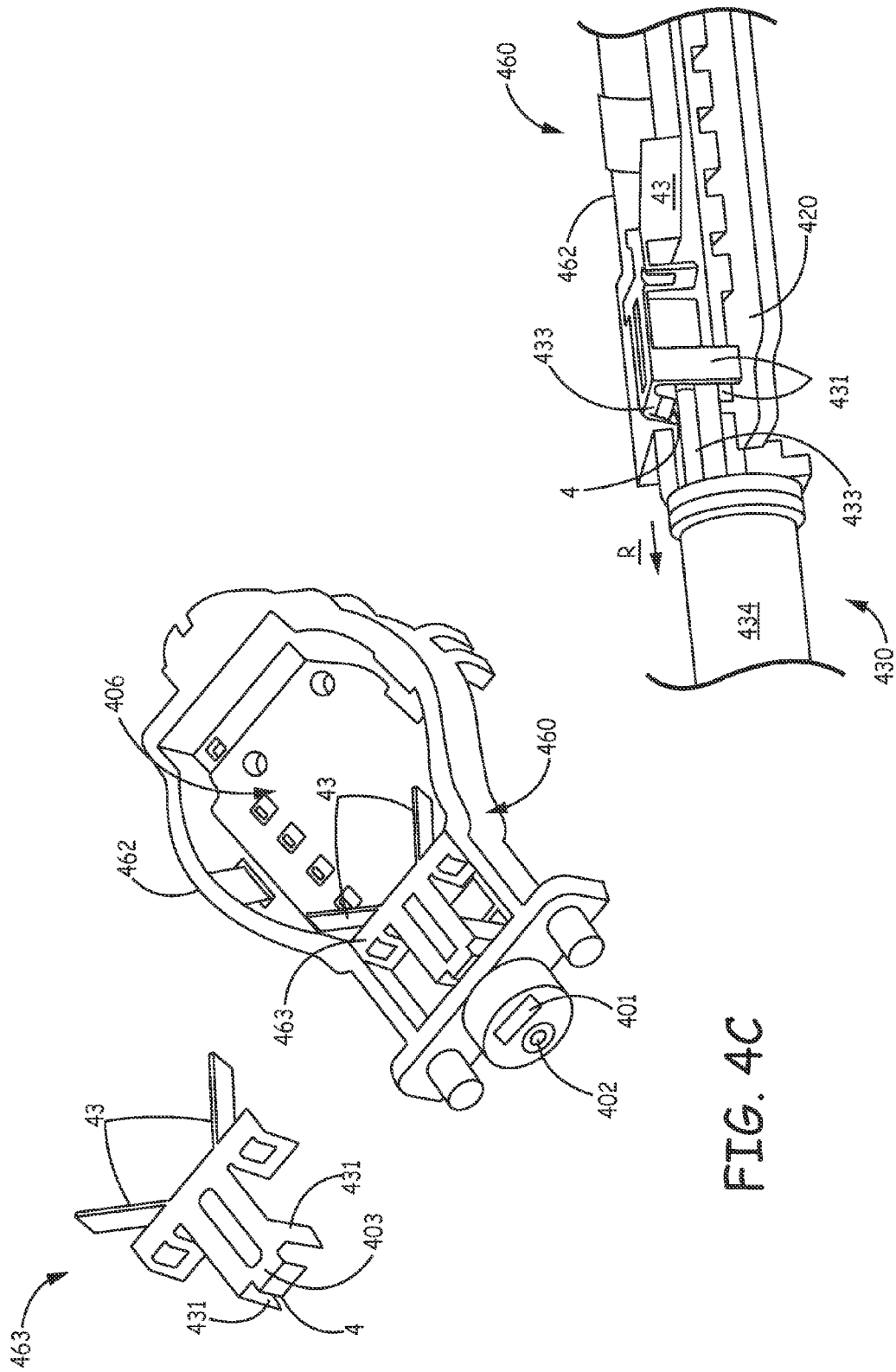

007
FILLING METHODS AND APPARATUS FOR IMPLANTED MEDICAL THERAPY DELIVERY DEVICES

The current application claims priority to U.S. patent application Ser. No. 13/426,045, filed Mar. 21, 2012, now pending, which is incorporated herein by reference in its entirety.

TECHNICAL FIELD

The present invention is related to implantable medical therapy delivery devices configured to be implanted in a body and to dispense therapeutic and/or diagnostic agents, and more particularly to associated apparatuses systems and methods for refilling an implanted medical delivery device.

BACKGROUND

Various types of implanted medical devices, such as implanted drug pumps, are used to deliver controlled volumes of a therapeutic fluid substance (e.g. a drug) within a patient's body. These pumps generally have reservoirs that may be accessed through ports, which may be self-sealing and may provide a drug suspension or solution from the device.

After the medical device is implanted within a patient, it may be desirable to fill, refill, flush out, or change fluid in a reservoir or other portion of the device. Typically, this is accomplished by a health care provider (HCP), for example, a clinician. The HCP typically locates the device access port by palpitating a patient's skin, as the access port typically protrudes from the infusion pump. The HCP then inserts a needle or similar device advancing through the patient's skin into the implanted device to dispense or remove the intended therapeutic fluid substance.

Because the implanted medical device cannot be directly viewed, care must be taken to ensure proper needle placement into the device before injecting a therapeutic substance. If the needle misses the device, the therapeutic substance may be dispensed in the patient's body resulting in delivery of an improper amount and at an improper location, with potentially adverse consequences for the patient.

SUMMARY

According to some embodiments of the present disclosure, transcutaneous filling apparatuses and systems are configured for use in methods for monitoring the transdermal insertion of the transcutaneous filling apparatus, for the purpose of filling a fill chamber of an implanted therapy delivery device, by measuring an impedance between each combination of pairs of conductive surfaces, or electrodes of a needle of the apparatus, and comparing each measured impedance to a threshold impedance. A measured impedance that is less than the threshold may be indicative of a closed circuit between the corresponding electrodes, and a measured impedance that is greater than the threshold corresponds may be indicative of an open circuit between the corresponding electrodes. It should be understood that as used in this disclosure, the term "open circuit" designates an intact circuit but for the presence of a non-conducting material that resists or impedes current flow, and is not meant to imply a circuit with a physical, actual gap or broken connection (disconnected wires). An open circuit for the purposes of this disclosure would result in higher measurable impedance, whereas a circuit that has a gap or disconnected wires would result in an unmeasurable impedance. The needle of the transcutaneous filling apparatus may include a piercing distal tip, for passing through a septum of the fill chamber, and a conduit extending along a length thereof through which agents are delivered to fill the fill chamber; and the aforementioned electrodes, at least three in number, are located on the needle.

According to some preferred methods and embodiments, the transcutaneous filling apparatus is configured to measure at least a first, second and third impedances, and to compare each impedance to a threshold, the first impedance being between a first electrode of the needle and a second electrode of the needle, the second impedance being between the second electrode and a third electrode of the needle, and the third impedance being between the first and third electrodes. In some embodiments, the second electrode is located on the needle so that, when the distal-most end of the needle has been inserted through a non-conductive septum to gain access to the fill chamber of the implanted device, the second electrode is located within the septum. Each of the first and third electrodes are located on a portion of the needle, and isolated from each other and the second electrode, so that, when the second electrode is located within the septum, all or a portion of each of the first and third electrodes will not be within the septum, but within a conductive medium, and the first and second measured impedances will be greater than the threshold impedance, and the third measured impedance will be less than the threshold impedance. In some embodiments, the apparatus is configured so that a confirmation signal is generated, when the measured first and second impedances are greater than the threshold impedance, and the measured third impedance is less than the threshold impedance, indicating that the second electrode of the apparatus is located within the non-conductive septum. In some embodiments the detection circuit is configured to generate a confirmation signal within one second of the second electrode being fully inserted within the nonconductive septum. In some embodiments, the apparatus is further configured to measure again at least the second impedance and to compare it to the threshold impedance, after generating the confirmation signal, and to continue generating the confirmation signal, if the second impedance is greater than the threshold impedance, but to generate a warning signal if the second impedance is less than the threshold impedance, a condition indicative of possible dislodgement of the fill apparatus needle from the fill chamber. In some embodiments, the detection circuit is configured to generate the warning signal within one second of the measurement of the second impedance that is less than the threshold impedance.

According to some embodiments of the present disclosure, a detection circuit, which is electrically coupled to each of the electrodes of the needle, and which may be removably attached to the needle, or contained within a hub assembly of the needle, is configured to measure and compare impedances, and to generate signals, as described above. Various configurations of electrodes, corresponding conductors, and associated electrical interconnects for coupling the electrodes to the detection circuit contained in the hub assembly are disclosed herein. It will be understood that the some modifications will need to be made in embodiments where the detection circuit is removably attached to the needle and not contained in an assembly of the needle, the needle in that embodiment being configured for connection to a syringe, via a hub, either formed or connected to the proximal end of the needle. According to some preferred embodiments, each electrode is electrically coupled by a pair of isolated conductors to the detection circuit, wherein each conductor of each pair of conductors includes an isolated terminal for electrical connection to the detection circuit, and the detection circuit is further configured to test electrical continuity through each pair of conductors.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 1A is an implant schematic depicting an exemplary implantable medical therapy delivery device;

FIG. 1B is a cross-section view of transdermal access to a fill chamber portion of the implanted device;

FIG. 4C is a perspective view, with an enlarged detail view, of a portion of the apparatus of FIG. 4A, according to some embodiments;

FIG. 4D is an enlarged detail view through a partial cutaway section of a portion of the apparatus;

DETAILED DESCRIPTION

Figure 2A:
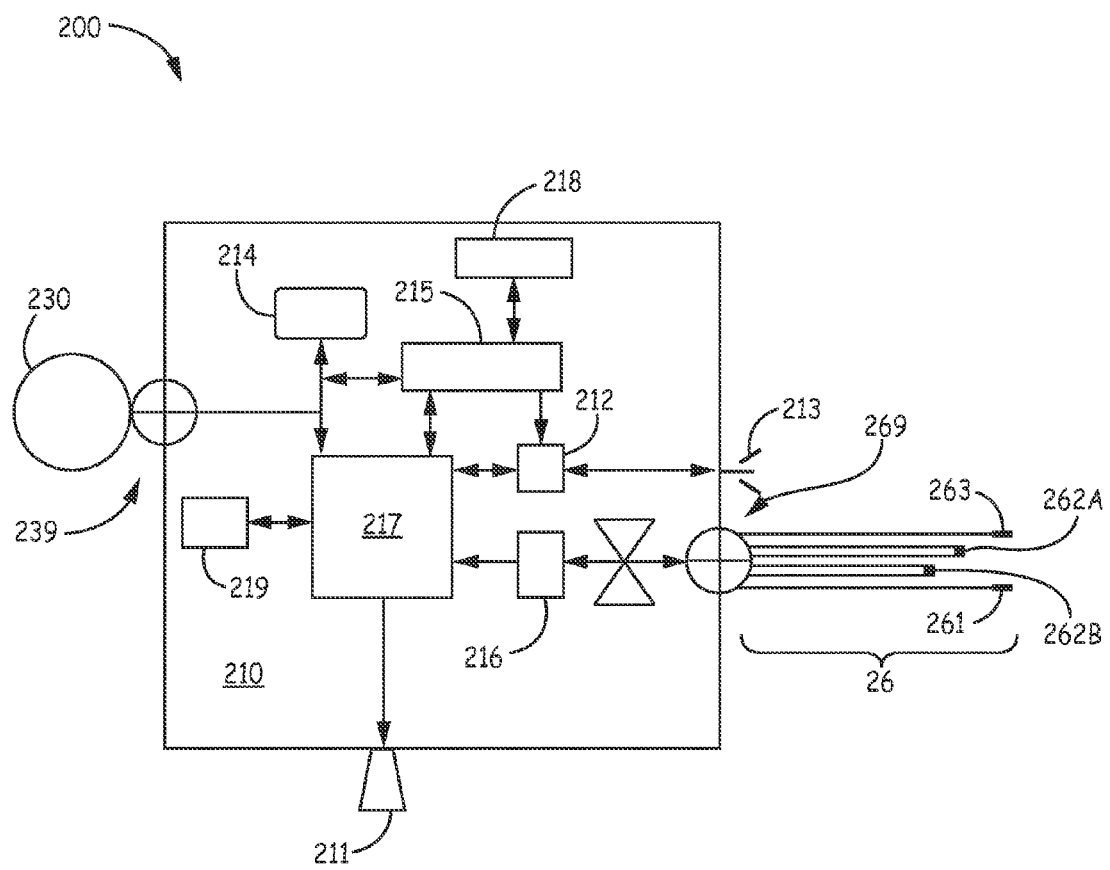
FIG. 2A is a schematic block diagram representation of a transcutaneous filling apparatus, according to some embodiments of the present disclosure.

The following detailed description is exemplary in nature and is not intended to limit the scope, applicability, or configuration of the invention in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

The present disclosure describes systems, devices and methods that can be used by a health care provider, patient or caregiver to fill or refill a reservoir of a therapy delivery device implanted subcutaneously in a patient with a drug or other therapeutic agent while providing feedback to the user regarding the location of the distal-most portion of a transcutaneous filling apparatus. One type of implantable medical therapy delivery device with which the systems, devices and methods disclosed herein may be used are infusion devices for the delivery of a drug or other liquid therapeutic agent.

FIG. 1A shows an implanted infusion device 12 having two port assemblies 40, 40' implanted in a patient. Infusion device 12 may include one, two, three, or any number of port assemblies. As shown in FIG. 1A, a catheter 34 is connected to infusion device 12. Distal portion 99 of catheter 34, which may have one or more openings through which fluid may flow, is positioned at or near a target location of a patient to deliver fluid from infusion device 12 to the target location. The target location depicted in FIG. 1A is the patient's intrathecal space surrounding the spinal canal. It will be understood, however, that any region of a patient's body may serve as a target location depending on the conditions, disease, or disorder to be treated. Port assemblies 40, 40' can be accessed percutaneously by a needle or other similar device (not shown in FIG. 1A), through which fluid may be delivered to infusion device 12.

Infusion device 12 may be any device capable of delivering liquid to a patient. For example, infusion device 12 may be an access port, e.g. a vascular access port, through which a solution or therapeutic substance from a needle may be delivered through a catheter to a patient, or may be a device having a reservoir (not shown) for holding solutions containing a therapeutic substance to be delivered over a period of time, such as devices with fixed or variable rate pumps, programmable pumps, or the like. Infusion devices having a reservoir will generally include a port assembly to allow for filling the reservoir.

Port assemblies 40, 40', shown in FIG. 1A, may for example respectively be a catheter access port and a fill port. As described in further detail below, fill port assembly 40 provides access to a reservoir 32 that retains a therapeutic substance. Exemplary devices having a catheter access port and a fill port include Medtronic's SYNCHROMED™ implanted infusion device, DePuy's CODMAN™ 3000 and OMT's LENUS PRO™ or other such implantable medical devices. Other exemplary implantable I.V. infusion port devices include Smiths Medical's PORT-A-CATH™ and P.A.S PORT™, and Bard Medical's POWERPORT™. Any currently known or future developed implanted infusion device can also be used.

FIG. 1B shows a cross-sectional view of a portion of infusion device 12 having a refill port 111, septum 112, a housing 114, and reservoir 118. FIG. 1B illustrates a needle 126 of a typical transcutaneous filling apparatus 160 inserted through skin 150, subcutaneous tissue 140, and into septum 112, so that a drug, for example, being injected from a syringe or other container of drug attached directly or indirectly, i.e., via a catheter or tubing, to a hub 116 of apparatus 160, can be delivered into chamber 110. The reservoir 118 may contain a therapeutic substance to be delivered to the patient, for example, via a catheter 34 (shown in FIG. 1A).

FIG. 2A is a schematic block diagram representation of a filling apparatus 200, according to some embodiments of the present disclosure, which includes a detection circuit 210, which is coupled, via needle contacts 269, to needle circuits 26, and a power source 230, for example, a coin cell battery, which is coupled to circuit 210 at contacts 239. FIG. 2A illustrates detection circuit 210 including an integrated circuit 217, which in this embodiment is a combined processor-impedance measurement circuit, coupled to supply filter capacitors 214, resistors 219 (reference load), and a 3V voltage regulator 215, which is coupled to an inductor 218; IC 217 receives input from needle contacts 269 through electrostatic discharge (ESD) protection diodes and DC block capacitors 216. The components of detection circuit may be mounted on a printed circuit board (PCB) or integrally formed into a molded member. One skilled in the art will know that detection circuit 210 may include a processor and an impedance circuit as separate components. In one embodiment, detection circuit may collect information about the impedance values of each of the electrodes when a confirmation or warning signal is generated and associated data about such events, for example, how much time elapsed following power up and the generation of the confirmation or warning signal, or time that elapsed between generation of a confirmation signal and a warning signal. The collected information may be stored in nonvolatile memory for transfer at a later time to another device such or transferred to another device having volatile or nonvolatile memory, wirelessly or by direct connection, upon collection.

According to the illustrated embodiment, needle circuits 26 include a first circuit for a first electrode 261, a pair of second circuits for one or more sets of second electrodes 262A, 262B, and a third circuit for a third electrode 263, wherein each circuit is electrically coupled to detection circuit 210 via a corresponding pair of contacts of needle contacts 269. A needle 260 that includes needle circuits 26 is shown schematically in FIGS. 2B-C. Although not explicitly shown, second electrodes 262A,B are located adjacent one another along a length of needle 260, so that the circuit of one of the pair may function as a redundant circuit to the other, in some embodiments, for example, like that described below, in conjunction with FIG. 6. According to alternate embodiments, needle circuits 26 include only a single second electrode 262 and corresponding circuit, and the following description that corresponds to FIGS. 2B-C makes reference to second electrode 262 in the singular. It should be noted that the circuit for first electrode 261 may be formed by a conductive wall 205 (FIG. 2B) of needle 260.

Figure 2B:
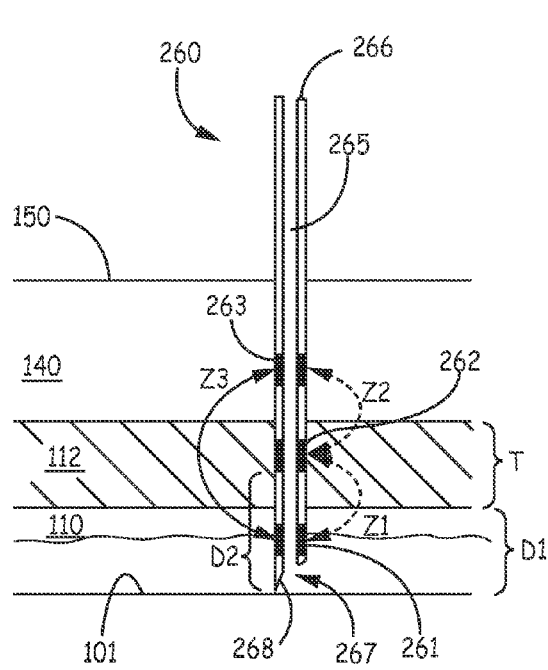
FIG. 2B is a schematic diagram of a needle portion of the filling apparatus transdermally inserted into the fill chamber of the implanted device.

FIG. 2B is a schematic diagram of needle 260 transdermally inserted into a fill chamber of an implanted device, for example, fill chamber 110 of device 12 (FIGS. 1A-B). FIG. 2B illustrates needle 260 including a piercing distal tip 267, which is terminated by a distal-most end 268 of needle 260, and a conduit 265 extending along a length of needle 260 (e.g. between approximately 1.5 inch (3.81 cm) and approximately 4.5 inches (11.43 cm)), from a proximal opening at a proximal end 266 of needle 260 to a distal opening in proximity to distal-most end 268. Distal tip 267 is shown having been passed through skin 150, subcutaneous tissue 140, and septum 112 to locate the distal opening of conduit 265 in fill chamber 100, for delivery of a therapeutic/diagnostic agent thereto. A conductive wall 205 of needle 260 is preferably relatively rigid, for example, being formed from stainless steel, and first electrode 261 is preferably formed by uninsulated portion of wall 205 that extends to distal-most end 268.

Needle 260 prior to the addition of any electrodes or insulating layers, may be, for example, a conventional hypodermic or infusion needle, or another instrument that may be capable of piercing through a patient's tissue and entering an implanted infusion device 12, and delivering therapeutic substance into reservoir 32. Needle 260 desirably is made from a conductive material such as a metal or a metallic alloy. In other embodiments a non-conducting needle may be made conductive by coating with suitable conductive material such as a metal, alloy, carbon black, conductive polymer or other conductive material. Exemplary conductive coatings include thin film conductive traces, conductive foils, and conductive deposits formed using thin-film deposition techniques such as vapor deposition, metal plating, PVD sputter deposition and the like. Suitable conductive materials include, for example, aluminum, copper, gold, silver, nickel, iron, stainless steel, nitinol, composite conductive polymers and the like.

Needle 260 has an inner and outer wall (shown as conductive wall 205 in FIG. 2B) each having inner and outer diameters. The inner wall defines conduit 265 through which the liquid therapeutic agent is delivered to the refill chamber. In some embodiments, needle 260 is a 22 gauge needle having an outer diameter (O.D.) of about 0.0280 inch (0.711 mm) and an inner diameter (I.D.) of about 0.0155-0.017 inch (0.394 mm-0.432 mm). In some embodiments, the needle has a needle length of greater than 2.0 inches (5.08 cm) the distal-most portion of the needle which will be inserted through the septum of the refill chamber during the refill process will have an O.D. and I.D. of a 22 gauge needle and the rest of the needle will have a larger O.D. and I.D. such as the O.D. and I.D. of a 19 or 20 gauge needle. In one embodiment, when the needle length is in the range of 4.0-4.5 inches (10.16-11.43 cm) the O.D. and I.D of the distal-most portion of the needle that may be inserted through the septum is approximately that of a 22 gauge needle and the O.D. and I.D. of the portion of the needle proximal to that portion will be approximately that of a 20 gauge needle. In yet another embodiment, the O.D. of the needle is larger at the proximal end and gradually decreases so that the O.D. at the distal-most portion of the needle that may be inserted through the septum is approximately that of a 22 gauge needle.

In FIG. 2B needle 260 is shown inserted to a maximum depth within fill chamber 110 so that distal-most end 268 touches a floor 101 of chamber 110, which, although not necessary for filling fill chamber 110, illustrates a condition that dictates a desired spacing of second and third electrodes 262, 263 relative to distal-most end 268, according to some embodiments. According to FIG. 2B: a distal edge of second electrode 262 is spaced from distal-most end 268 by a distance D2 that is greater than a distance D1 between septum 112 and floor 101, to prevent second electrode 262 from entering into chamber 110; a length of second electrode 262, between the distal edge and a proximal edge thereof, is less than a thickness T of septum 112, to assure that the entire length thereof is contained within septum 112, when distal tip 267 of needle 260 is positioned in chamber 110 at a sufficient depth for filling chamber 110; and a distal edge of third electrode 263 is spaced from distal-most end 268 by a distance D3 that is greater than thickness T added to distance D1, to assure that none of third exposed surface 263 enters into septum 112 when needle 260 is inserted to the maximum depth illustrated in FIG. 2B.

In some alternate embodiments, not shown in the Figures, first and third electrodes 261, 263 may both be positioned proximal to second electrode, so that when second electrode 262 is within non-conductive septum 112 and distal-most end 268 of the needle is in fill chamber 110, at least a portion of each of the first and third electrodes will be located in a conductive medium, either subcutaneous tissue 140, or fill chamber 110. Electrodes 261, 262, 263 are all generally located along a distal portion of needle 260, which is distinguished from a proximal portion thereof that remains outside the body during the filling process and has needle contacts 269 formed thereon for coupling to detection circuit 210. Some alternative embodiments of needle circuits 26, which include electrodes 261, 262, 263 and needle contacts 269, and the conductors extending therebetween, will be described below in conjunction with FIGS. 5-9.

Detection circuit 210 (FIG. 2A) is configured to measure an impedance between each combination of pairs of electrodes 261, 262, 263, and then to compare each of the measured impedances to a threshold impedance. The threshold impedance is set at a value that is sufficiently greater than that of tissue that surrounds the implanted device and corresponds to electrical isolation of any of electrodes 261, 262, 263 from the others, when contained within septum 112 of the device. According to some embodiments, the threshold impedance is set to between approximately 10,000 and 100,000 Ohms, and in one embodiment the threshold impedance is set to approximately 20,000 Ohms, and IC 217 measures each of the three impedances, at a separate frequency, and then compares each to the threshold. According to some preferred embodiments, detection circuit 210 is further configured to generate signals, a visual type and/or an audible type, based upon the measured impedances (described below in conjunction with FIGS. 2B-3), so FIG. 2A further illustrates detection circuit 210 including an audible signal generator 211 and a visual signal generator, for example, an LED driver 212 and an associated bi-color LED 213, or separate single-color LEDs, transmitted through a light pipe. Another single-color LED and associated light pipe (not shown) may be coupled to IC 217 to generate another light signal of a different color that indicates IC 217 is powered up and apparatus 200 is ready for use.

According to some embodiments, the detection circuit is configured to generate a confirmation signal within one second of the second electrode being fully inserted within the nonconductive septum. In some embodiments the apparatus is further configured to measure again at least the second impedance and compare it to the threshold impedance after the confirmation signal is generated and continue generating the confirmation signal if the second impedance is greater than the threshold impedance but to generate a warning signal if the second impedance subsequently becomes less than the threshold impedance, a condition indicative of possible dislodgement of the fill apparatus needle from the fill chamber. In some embodiments, the detection circuit is configured to generate the warning signal within one second of this condition being detected.

According to some embodiments, detection circuit 210 may be removably attached to needle 260, or contained within a housing or hub assembly attached to the proximal portion of needle 260. An exemplary embodiment of a hub assembly 410, which supports detection circuit 210, power source 230 and signal generators 211, 213, is described below in conjunction with FIGS. 4A-E.

With further reference to FIG. 2B, impedances measured between each combination of pairs of electrodes 261, 262, 263, are represented with double-headed arrows. A dashed double-headed arrow is used to designate each of a first impedance Z1 and a second impedance Z2, both greater than the aforementioned threshold impedance; and a solid double-headed arrow is used to designate a third impedance Z3 that is less than the threshold impedance. First and second impedances Z1, Z2 are greater than the threshold, because second electrode 262 is electrically isolated within septum 112, which is formed by a non-conductive or insulative material, for example, silicone rubber; and third impedance is less than the threshold because both first and third electrodes 261, 263 are located within a conductive medium or environment—first electrode 261 within liquid contained by fill chamber 110 and/or contacting floor 101 of fill chamber 110, which is preferably conductive, and third electrode 263 within the tissue 140 surrounding the implanted device. According to an alternate embodiment, first and third electrodes 261, 263 may both be positioned proximal to second electrode 262, along the distal portion of needle 260, to be located in the conductive medium of tissue 140. In either case, when detection circuit 210 measures impedances Z1, Z2, Z3 and compares them to the threshold impedance, circuit 210 confirms that needle 260 is properly positioned to fill chamber 110, for example, with a confirmation signal from one or both of signal generators 211, 213 of FIG. 2B.

Figure 2C:
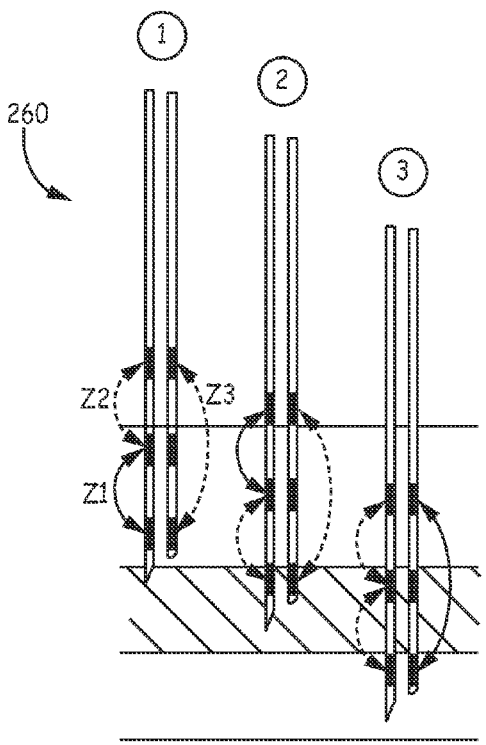
FIG. 2C is a schematic diagram of progressive insertion of the needle into the fill chamber.
Figure 3:
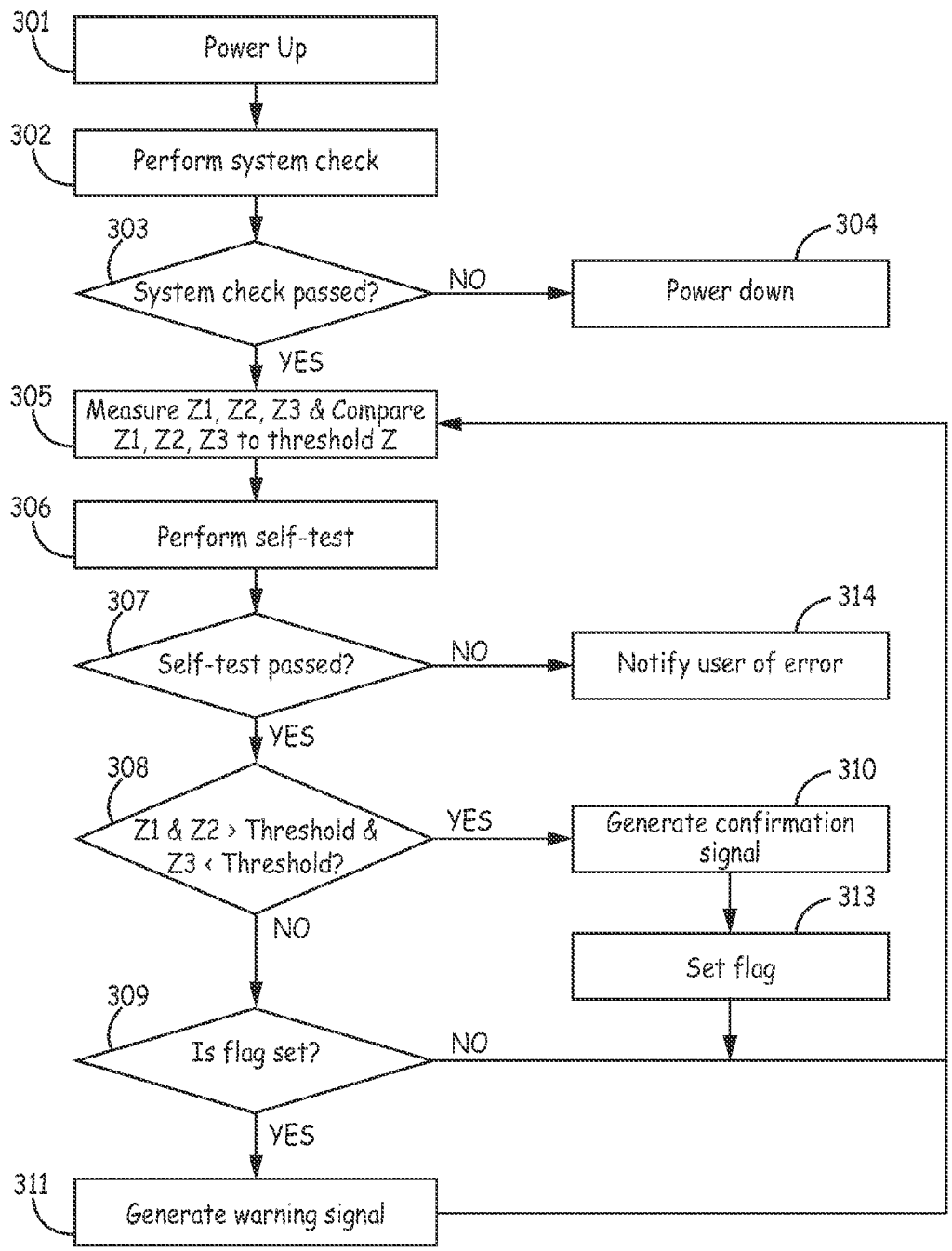
FIG. 3 is a flow chart outlining steps according to preferred methods of the present disclosure.

FIG. 2C is a schematic diagram of progressive insertion of needle 260 into fill chamber 110, for reference in conjunction with the flow chart of FIG. 3, which outlines steps for monitoring transdermal insertion of transcutaneous fill apparatus 200. With reference to FIG. 3, prior to insertion, an operator powers up fill apparatus 200, per step 301, at which time a power-on light signal may be generated by detection circuit 210, via the other single-color LED and associated light pipe mentioned above. Also, upon power up and prior to insertion, according to some methods, apparatus 200 conducts a system self-check, per step 302, in which detection circuit 210 performs checks of components of apparatus 200 to ensure that the apparatus is fully operational and all electrode combinations are functioning correctly. If the system check determines that the apparatus is not fully operational (decision point 303), a warning signal may be generated or the apparatus may shut down, per step 304. If the system self-check is passed (decision point 303), the operator may commence transdermal insertion of the transcutaneous fill apparatus 200 into the patient while detection circuit 210 measures impedances Z1, Z2 and Z3 and compares each to the threshold impedance, per step 305, and a self-test is performed, per step 306, to determine whether all the electrode combinations are functioning correctly, at decision point 307. Upon confirmation of operational integrity (303), detection circuit 210 may generate a different type of audible and/or light signal as a signal to the operator. According to some embodiments, the self-test of step 306 is conducted via a continuity check of redundant conductors for each electrode 261, 262, 263, which are shown in circuits 26 of FIG. 2A. If the self-test fails, apparatus 200 notifies the user/operator, per step 314, for example, by generating an audible and/or light warning signal, for example, via one or both of signal generators 211, 213, and then powering down; alternately, at step 314, apparatus 200 may simply power down and turn off the aforementioned optional power up light signal.

FIG. 2C shows three positions 1, 2, and 3 of needle 260 in the process of insertion. With reference to decision point 308 of FIG. 3, detection circuit 210 measures impedances Z1, Z2, and Z3 and compares each to the threshold impedance throughout the insertion of the apparatus and delivery of the liquid therapeutic agent. Measurements and comparisons of Z1, Z2, Z3, at, and between positions 1 and 2 will not generate any signal unless the apparatus fails the self-test performed after the comparison of the measurements to the threshold has been. When measurements and comparisons of Z1, Z2, Z3 indicate that Z1 and Z2 are each greater than the threshold value, and that Z3 is less than the threshold value, for example, corresponding to position 3 in FIG. 2C, a confirmation signal, for example, a green light that may be accompanied by a tone, is generated, per step 310. The confirmation signal may be any audible or visual signal or combination thereof that will let the operator of the apparatus know that the needle is in the refill chamber and that the operator can commence the refill process, for example, by first aspirating residual contents of device reservoir 118 (FIG. 1B), and then connecting fill apparatus 200 to another reservoir of therapeutic/diagnostic agent, and then beginning to deliver the agent from the reservoir through conduit 265 of needle 260 and into fill chamber 110 of device. According to some embodiments, the detection circuitry 210 may be operatively integrated with a valve mechanism that prevents flow of substance through needle 260 prior to the confirmation at step 310.

With further reference to FIG. 3, upon generation of the first confirmation signal during the insertion process, per step 310, a flag is set to "1" or equivalent, per step 313. During the insertion process, and prior to reaching position 3 (corresponding to steps 310 and 313), for example, when needle 260 is at positions 1 and 2 of FIG. 2C, circuit 210 checks for a flag setting at decision point 309, and since no flag has been set, prior to reaching position 3, circuit 210 continues to measure and compare impedances, per step 305, and perform the self-test, per step 306. After steps 310 and 313, when needle 260 is properly inserted into fill chamber 110 for the filling process, circuit 210 also continues to perform steps 305 and 306 in order to monitor the continued insertion of needle 260, and detect if needle 260 becomes dislodged during the filling process. If, after the confirmation signal is generated and the flag set (steps 310, 313), impedances Z1, Z2, and Z3 do not meet the threshold criteria of decision point 308, circuit 210 will detect that a flag has been set and that subsequently the system detected a condition as represented in the left-most and center needle positions in FIG. 2C, per decision point 309, and generate a warning signal, per step 311, that notifies the operator that needle 260 has become dislodged, and to stop the filling process. The second warning signal is preferably a light signal, for example, steady or flashing red, which may be accompanied by an audible tone. Alternately, or in addition, one or both of the aforementioned mechanisms operably coupled to circuit 210 may be triggered at step 311 to stop the flow through needle 260. In another embodiment, in order to ensure the safety of the patient the filling apparatus is configured for a single-use and once the apparatus has been powered up and powered down if a user powers up the apparatus a second time the detection circuit will check to see if the apparatus was powered up before and if so it will immediately shut down the apparatus.

Figure 4A:
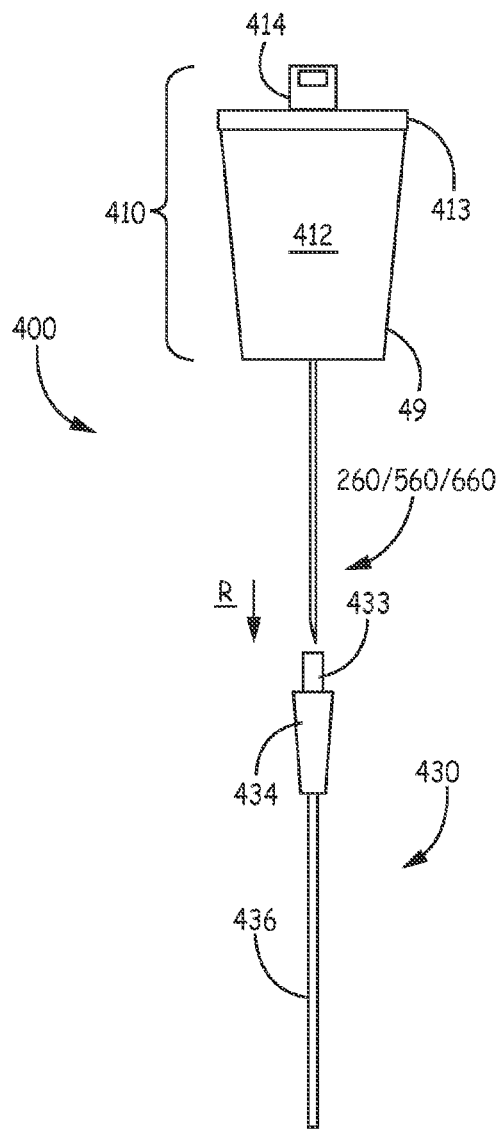
FIG. 4A is a plan view of a transcutaneous filling apparatus, according to some embodiments.

Turning now to FIGS. 4A-D, the aforementioned hub assembly 410 and associated exemplary electrical interconnect features will be described. FIG. 4A is a plan view of a filling apparatus 400, wherein hub assembly 410 is attached to the proximal portion of needle 260. FIG. 4A illustrates hub assembly 410 including a housing 412 and a cap 413 having a hub 414 through which a port is formed; the port of hub 414 is in fluid communication with conduit 265 of needle 260, and hub 414 is configured to fluidly connect needle 216 to a syringe (not shown) that contains a therapeutic substance in liquid form. Hub 414 may, for example, include luer connector features, or the like. Hub 414 may be formed from metal or polymer materials such as Acrylonitrile Butadiene Styrene (ABS), polystyrene, polyvinyl chloride, polysulfone or other suitable material. According to the illustrated embodiment, and with reference back to FIG. 2A, housing 412 contains IC 217, power source 230 and needle contacts 269. FIG. 4A further illustrates apparatus 400 including a protective needle guard 430 having been removed from around needle 260, per arrow R. Needle guard 430 is shown including a shaft portion 436, configured to contain the distal portion of needle 260, a gripping portion 434 and a battery tab 433, which will be described in conjunction with FIG. 4C.

Figure 4B:
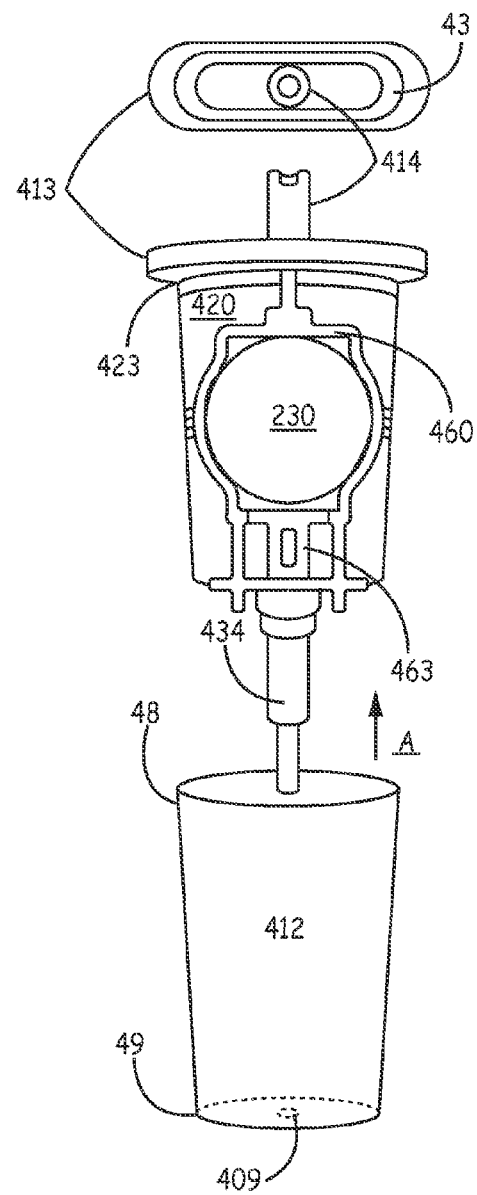
FIG. 4B is an exploded perspective view, alongside a top view, of the apparatus of FIG. 4A, according to some embodiments.

FIG. 4B is a top view of apparatus 400, alongside an exploded view of apparatus 400, wherein housing 412 is separated from cap 413 and hub 414 to show a printed circuit board (PCB) 420, which encompasses IC 210, and battery power source 230 stacked and coupled together via an electrical interconnect assembly 460, which is connected to cap 413. In a preferred embodiment housing 412 is molded as one piece without any seams. According to the illustrated embodiment, a proximal end 48 of housing 412 surrounds an opening thereof that receives battery 230, PCB 420, and electrical interconnect assembly 460 into a cavity thereof. When housing 412 is assembled around battery 230, PCB 420, and electrical interconnect assembly 460, for example, by moving housing 412 per arrow A, around needle 260 and needle guard 430, which extend out through a distal opening 409 of housing 412, the opening at proximal end 48 of housing 412 mates with a sealing interface 423 of cap 413; the mating interface may be secured, for example, by snap-fit, a crush feature, adhesive bonding and/or ultrasonic welding according to methods known in the art. The assembly of cap 413 together with housing 412 is preferably water resistant. With reference to the top view of apparatus 400 in FIG. 4B, all or a portion 43 of cap 413 may be translucent, so that the aforementioned light signals may be projected therethrough. Furthermore, a relatively small aperture may be formed in housing 412 for the projection of the aforementioned audible signals, for example, with reference to FIGS. 4A-B, being located in proximity to an opening 409 at a distal end 49 of housing 412 from which needle 260 extends. Housing 412, cap 413 and needle guard 430 may be formed from any suitable relatively rigid material, such as such as Acrylonitrile Butadiene Styrene (ABS), polystyrene, polyvinyl chloride, polysulfone, polypropylene, polyurethane, polyethylene or any other suitable material known to those skilled in the art.

FIG. 4C is a perspective view of interconnect assembly 460. FIG. 4C illustrates interconnect assembly 460 including an insulative carrier 462, for example, being formed from a relatively rigid material, such as Acrylonitrile Butadiene Styrene (ABS), polystyrene, polyvinyl chloride, polysulfone or any other suitable material known to those skilled in the art. FIG. 4C further illustrates carrier 462 including a cavity 406 formed therein to receive battery 230, and a battery connector 463, for example, a stamped beryllium copper, or stainless steel component, supported by carrier 462; flexible contact arms 43 of battery connector 463 are located in cavity 406 to make electrical contact with battery 230, when battery 230 is inserted therein. An enlarged view of battery connector 463, separate from carrier 462, is also shown in FIG. 4C, so that another pair of contact arms 431 may be seen in conjunction with a tab member 403 of connector 463. With reference to FIG. 4D, which is an enlarged view through a partial cut-away section of a portion of hub assembly 410, tab member 403 extends into carrier 462 to be located within a receptacle 401. When needle guard 460 is fitted around needle 260, as illustrated in FIG. 4B, battery tab 433 of needle guard 460 is located in receptacle 401 and engages tab member 403 to lift contact arms 431 away from corresponding contact pads (not shown) formed on PCB 420, thereby preventing contact arms 431 from making electrical contact with detection circuit 210. Thus, apparatus 400 does not become powered up for operation until an operator, for example, by grasping around gripping portion 434, removes needle guard 460 from around needle 260 (per arrow R, FIGS. 4A and 4D), thereby pulling tab 433 out of engagement with tab member 403 to allow contact arms 431 of battery connector 463 make contact the corresponding contact pads on PCB 420. According to some embodiments, an end 4 of tab member 403 of connector 463 is configured, for example, bends toward the opening of receptacle 401, to prevent an operator from reinserting battery tab 433 of needle guard 430 back into engagement with tab member 403, thereby preventing a preservation of battery life, by breaking electrical contact with PCB 420, for the reuse of apparatus 400, since apparatus 400 is preferably a sterilized single-use and disposable apparatus.

Figure 4E:
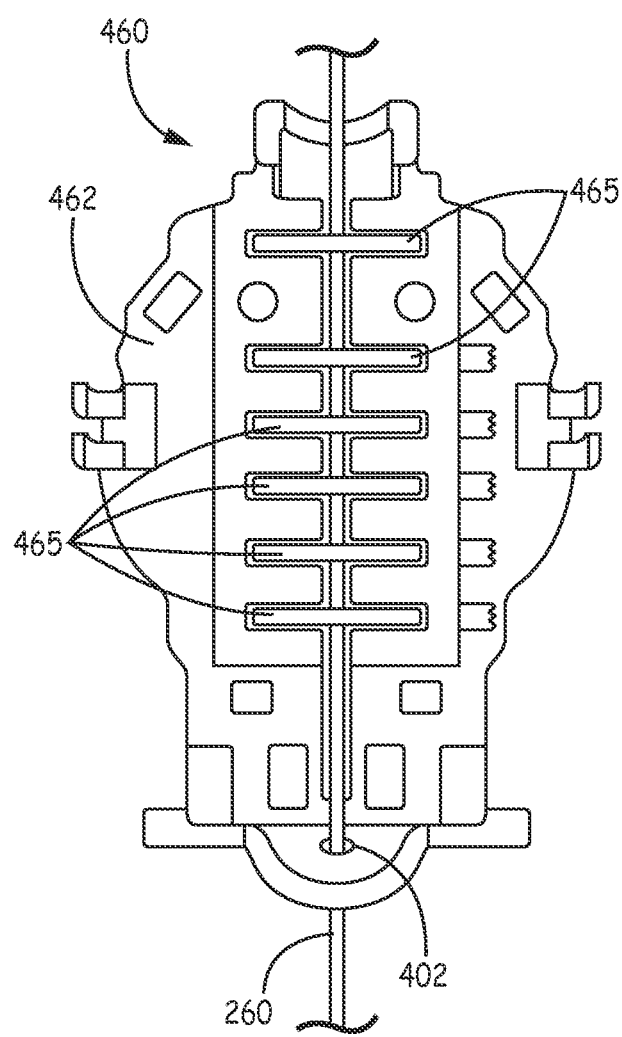
FIG. 4E is a plan view of the portion of the apparatus shown in FIG. 4C, according to some embodiments.

FIG. 4E is a plan view of interconnect assembly 460, showing an opposite side thereof from that shown in FIG. 4C, wherein the side shown is that which interfaces with PCB 420 (FIG. 4B), according to some embodiments. FIG. 4E illustrates the proximal portion of needle 260 extending within a channel 402 of interconnect assembly 460. FIG. 4E further illustrates carrier 462 supporting an array of needle contacts 465, for example, a leaf spring-type, which are spaced apart and isolated from one another along a length of channel 402 and proximal portion of needle 260. According to the illustrated embodiment, each contact 465, for example, an end thereof, makes contact with a corresponding contact pad on PCB 420, for example, being soldered thereto or in mechanical contact with, when interconnect assembly 460 is assembled together with PCB 420 in housing 412, so that needle circuits 26 are coupled to PCB 420 by a central portion of each contact 465 making contact with a corresponding one of contacts (not shown) that are formed along the inserted proximal length of needle 260. According to some alternate embodiments, PCB 420 includes commercially available surface mounted contacts that align to and make electrical contact with the contacts that are formed along the inserted proximal length of needle 260 when the PCB is assembled to the carrier.

Figure 5:
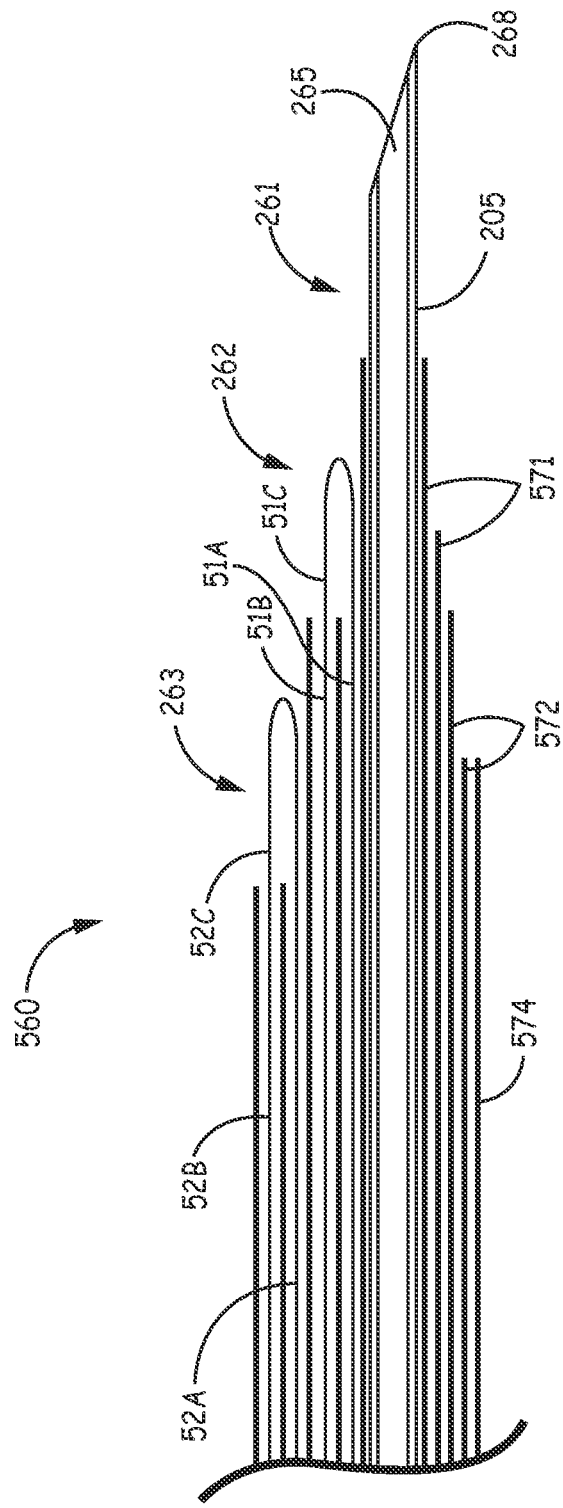
FIG. 5 is a longitudinal cross-section view of a distal portion of a needle that may be employed by the transcutaneous filling apparatus, according to some embodiments.
Figure 6:
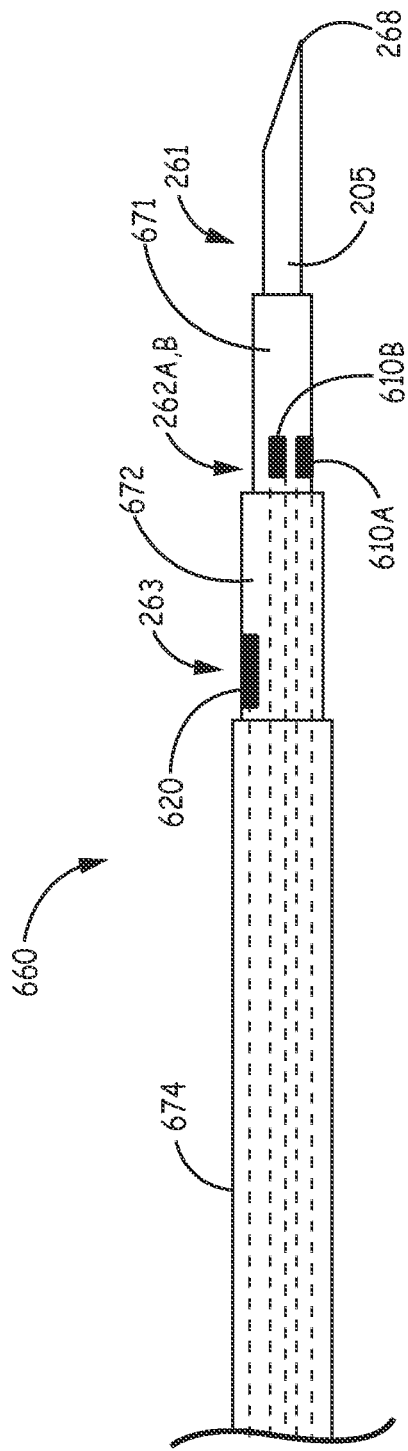
FIG. 6 is a plan view of a distal portion of a needle that may be employed by the transcutaneous filling apparatus, according to some alternate embodiments.
Figure 7:
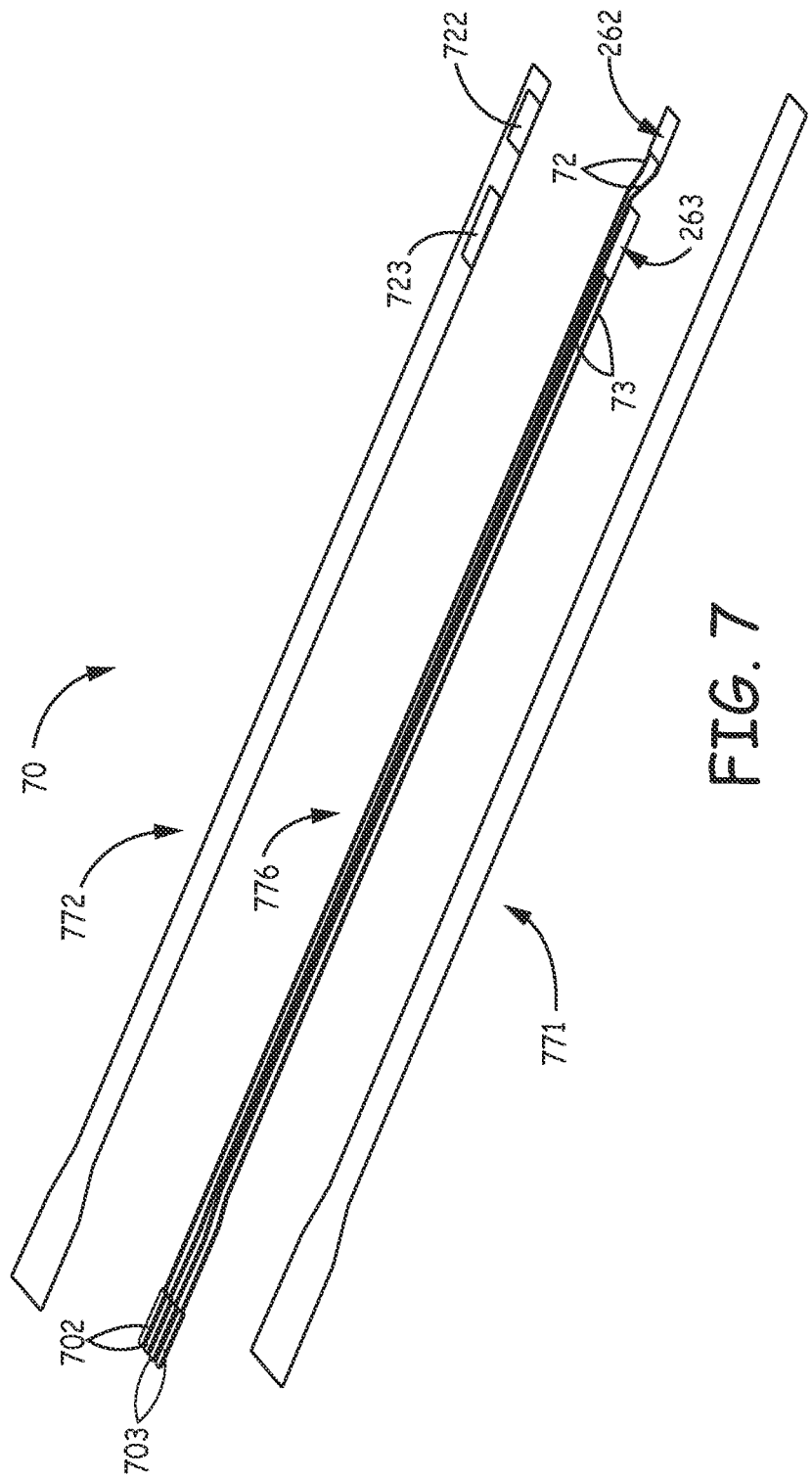
FIG. 7 is an exploded perspective view of a flex circuit assembly that may be employed by the transcutaneous filling apparatus, according to yet further embodiments.
Figure 8:
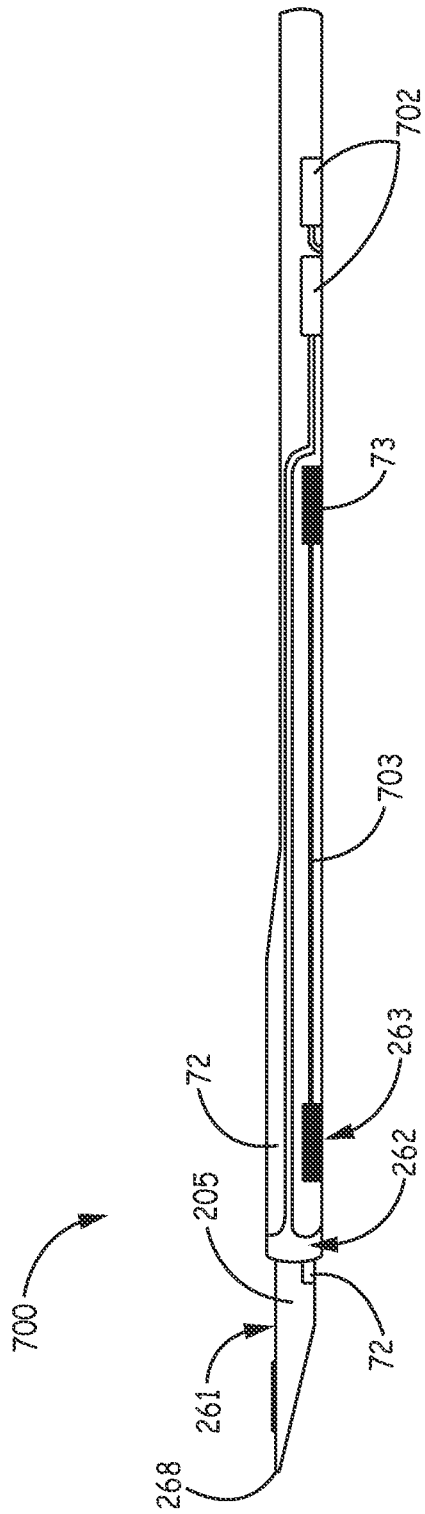
FIG. 8 is a plan view of a portion of a needle including a configuration of the flex circuit assembly, according to some embodiments.
Figure 9:
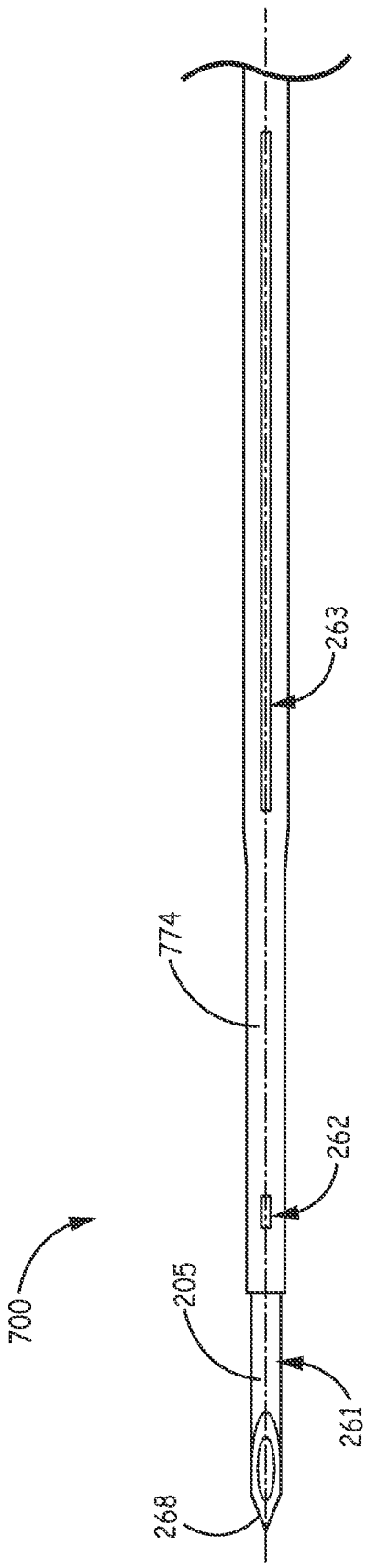
FIG. 9 is a plan view of a distal portion of a needle that may be employed by the filling apparatus, according to some embodiments.

Each contact formed on the proximal length of needle 260 corresponds to one of electrodes 261, 262, 263, and is coupled thereto by a corresponding conductor, or pair of redundant conductors, as described in greater detail below. As indicated above, various configurations of needle circuits 26 may be employed by apparatus 200/400. Alternate embodiments are described below in conjunction with FIGS. 5-9. FIG. 5 illustrates an exemplary embodiment that employs insulated fine wires; FIG. 6 illustrates an exemplary embodiment that employs conductive ink traces patterned onto one or more conductive layers; and FIGS. 7-9 illustrates exemplary embodiments that employ a flex circuit assembly.

FIG. 5 is a longitudinal cross-section view of a distal portion of a needle 560, which may be employed by transcutaneous filling apparatus 200/400, according to some embodiments. FIG. 5 illustrates needle 560, like needle 260, including conductive wall 205 that has a portion, extending proximally from distal-most end 268, that is uninsulated to form first electrode 261. FIG. 5 further illustrates needle 560 including first and second conductive wires that each have an insulated first segment 51A, 52A, an insulated second segment 51B, 52B, and a third segment 51C, 52C that extends between the corresponding first and second segments and forms the corresponding electrode 262, 263. It should be noted that electrodes 262, 263 may each be formed by a conductive ring member that extends around a perimeter of needle 560 and is coupled to the corresponding wire segment 51C, 52C.

According to the illustrated embodiment, first segment 51A of the first wire is insulated between a first pair of nonconductive layers 571 that overlay conductive wall 205, and second segment 51B of the first wire is insulated between an outer surface of first pair 571 and an inner surface of a second pair of nonconductive layers 572 that overlay first pair 571; and first segment 52A of the second wire is insulated between the second pair of nonconductive layers 572, and second segment 52B of the second wire is insulated between an outer surface of second pair 572 and an outer insulation layer 574. Proximal ends of wire first and second segments 51A, 52A, 51B, 52B each form isolated terminals located in proximity to needle proximal end 266 for electrical coupling to contacts of any of interconnect assemblies 460, 480, 860, 960, as described above.

The conductive wires of needle 560 may be formed from any suitable conductive and biocompatible metal, such as stainless steel, gold, silver or MP35N alloy, known to those skilled in the art, and may have a diameter of between approximately 0.001 inch and 0.003 inch. First and second pairs of nonconductive layers 571, 572 as well as outer insulation layer 574 are preferably formed from a polyethylene terephthalate (PET) heat shrinkable material, known in the art but any biocompatible insulative material may be used, that may have a wall thickness between approximately 0.0005 inch and 0.001 inch. The extensions of wire segments 51A, 52A, 51B, 52B to proximal end 266 of needle 560 may be relatively straight, or wound about conductive wall 205 in a helical fashion.

In alternate embodiments, not shown in the Figures, two insulated conductive wires of differing lengths are attached to the sides of a needle using an adhesive material or other mechanical connector wherein the insulation on the top surface of a portion of the wire is removed to form an electrode at a desired location.

FIG. 6 is a plan view of a distal portion of a needle 660, which may be employed by transcutaneous filling apparatus 200/400, according to some alternate embodiments. FIG. 6 illustrates needle 660, like needle 560, including conductive conductive wall 205, which has an uninsulated portion, in proximity to distal-most end 268, to form first electrode 261. FIG. 6 further illustrates needle 660 including a nonconductive layer 671, an optional second nonconductive layer 672, which overlays nonconductive layer 671, and an outer insulation layer 674. A pair of redundant second electrodes 262A,B are formed by conductive layers 610A,B deposited on first nonconductive layer 671, and third electrode 263 is formed by conductive layer 620 which is shown deposited on optional second layer 672, but may be deposited on first nonconductive layer 671, according to some alternate embodiments. According to the illustrated embodiment, a pair of redundant conductive traces (shown with dashed lines) couple each conductive layer 610A, 610B to a corresponding pair of isolated contacts, and another conductive trace couples conductive layer 620 to a corresponding contact, wherein all of the contacts are spaced apart and isolated from one another along the proximal portion of needle 560 (not shown) for electrical coupling with the aforementioned surface mounted contacts (not shown) on PCB 420 within housing 412 (FIGS. 4A-B), or with array of needle contacts 465 of interconnect assembly 460 (FIG. 4E). Although not necessary, redundant second electrodes 262A,B provide a backup if one of electrodes 262A,B is damaged during the above described insertion into the fill chamber of an implanted device; furthermore, redundant conductive traces for each of electrodes 262A,B allows for a continuity check of the traces, according to the above-described self-test.

FIG. 6 shows conductive layers 610A, 610B exposed just distal to a distal terminal edge of optional second nonconductive layer 672, and the corresponding conductive traces being isolated beneath second nonconductive layer 672; and second conductive layer 620 is shown exposed just distal to a distal terminal edge of outer insulation layer 674, to form third electrode 263, with the corresponding conductive trace isolated beneath outer insulation layer 674. However, according to the aforementioned alternate embodiments, all of conductive layers 610A, 610B, 620 and the corresponding traces may be formed on a single nonconductive layer, e.g. layer 671, and then overlaid with outer insulation layer 674, wherein openings may be formed through layer 674, either before or after assembling layer 674, to expose conductive layers 610A, 610B, 620 for electrodes 262A,B, 263. In an alternate embodiment a liquid non-conductive coating may be applied over conductive layers leaving exposed areas of conductive layers where required.

According to an exemplary embodiment, non-conductive layer 671 is formed from the aforementioned PET heat shrinkable material, and a conductive silver ink (e.g., available from Micropen Technologies Corp. of Honeoye, N.Y.) is deposited on nonconductive layer 671 to form conductive traces 610A,B, 620 and the corresponding conductive traces, according to methods known to those skilled in the art. According to some alternate embodiments, first non-conductive layer 671 may be formed of a dip-coated, or an inked-on layer of polyimide or similar non-conducting material. Outer insulation layer 674, and optional nonconductive layer 272, may be formed from the PET heat shrinkable material, or may be a dielectric material, such as polyimide or other non-conductive material, deposited in the same fashion as the conductive ink, or applied in a dip process, according to methods known in the art.

FIG. 7 is an exploded perspective view of a flex circuit assembly 70 that forms a portion of yet another needle embodiment, which may be employed by transcutaneous filling apparatus 200/400. FIG. 7 illustrates assembly 70 including an first insulation layer 771, a second insulation layer 772, and a flexible circuit 776, preferably copper, which is located for sandwiching between layers 771, 772, when assembly 70 is included in a needle assembly. FIG. 7 further illustrates flexible circuit 776 including second and third electrodes 262, 263 and corresponding pairs of conductors 72, 73 for coupling electrodes 262, 263 to detection circuit 210. According to the illustrated embodiment, first insulation layer 771 overlays and conforms to needle conductive wall 205, for example, being bonded thereto, and isolates circuit 776 from conductive wall 205, which, like needles 560 and 660, is conductive to form first electrode 261 in proximity to distal-most end 268; furthermore, second insulation layer 772 overlays circuit 776 to secure circuit 776 in place, and to isolate electrodes 262, 263 and corresponding conductors 72, 73 from one another. According to an exemplary embodiment, first and second insulation layers 771, 772 are each formed of polyimide and are secured to one another via an adhesive layer formed over facing surfaces. It should be noted that assembly 70 may be constructed according to methods known to those skilled in the art of flex circuit assemblies. Each conductor of each pair 72, 73 is shown extending between the corresponding electrode 262, 263 and a corresponding pair of isolated contact terminals 702, 703, which are located at a proximal end of assembly 70, and which may be arranged in-line along the proximal portion of a needle 700, when assembly 70 is assembled around needle wall 205, for example, as illustrated in FIG. 8. The illustrated in-line arrangement of contact terminals 702, 703 facilitates electrical coupling to the aforementioned surface mounted contacts (not shown) on PCB 420 within housing 412 (FIGS. 4A-B), or with array of needle contacts 465 of interconnect assembly 460 (FIG. 4E). According to the illustrated embodiment, a continuity check of each pair of conductors 72, 73 may be carried out for the above-described self-test.

With further reference to FIG. 7, second insulation layer 772 of flex circuit assembly 70 has apertures 722, 723 located to expose electrodes 262, 263. FIG. 9 is a plan view of a distal portion of needle 700, according to some embodiments, wherein a outer insulation layer 774, for example, formed from the aforementioned PET shrink material, overlays flex circuit assembly 70, and includes openings formed therethrough, for example, being laser ablated, to expose electrodes 262, 263. An outer insulation layer 774, for example, formed from the aforementioned PET shrink material, may overlay flex circuit assembly 70, for example, having a distal terminal edge located in proximity to a proximal edge of third electrode 263.

In the foregoing detailed description, the invention has been described with reference to specific embodiments. However, it may be appreciated that various modifications and changes can be made without departing from the scope of the invention as set forth in the appended claims.

The invention claimed is:

1. A filling apparatus for use by an operator in delivering a liquid therapeutic agent into a refill chamber of a therapy delivery device through a non-conductive septum of the refill chamber wherein the septum, refill chamber and therapy delivery device are implanted subcutaneously in a patient, the apparatus comprising:
a needle comprising a proximal end, a distal portion, a distal-most end having a piercing distal tip, a conduit extending along the needle, from a proximal opening at the proximal end to a distal opening located in proximity to the distal-most end, and a connector at the proximal end configured to connect to a syringe containing the liquid therapeutic agent, first, second and third electrodes located on the distal portion of the needle so that when the distal-most end of the needle is inserted through the septum and in the refill chamber the second electrode is located within the septum and wherein each of the first electrode is spaced distally or proximally from the septum and the third electrode is spaced proximally from the septum;
a detection circuit attached to the proximal end of the needle and electrically coupled to the first, second and third electrodes of the needle, the circuit configured to measure a first impedance between the first and second electrodes, a second impedance between the second and third electrodes, and a third impedance between the first and third electrodes, and to compare each of the measured impedances to a threshold impedance as the needle is being guided through the patient's tissue to the refill chamber, and the circuit is further configured to generate a confirmation signal when the first and second measured impedances are greater than the threshold impedance and the third measured impedance is less than the threshold impedance, the signal indicating to the operator that the second electrode is within the septum and the distal-most end of the needle is in the refill chamber and the liquid therapeutic agent can be delivered.

2. The apparatus of claim 1, wherein the detection circuit is further configured to continuously measure the first, second, and third impedances after the confirmation signal is generated and if either first or second measured impedance is less than the threshold impedance or the third measured impedance is greater than the threshold impedance indicating dislodgment of the second electrode from the septum the confirmation signal is stopped and a warning signal is generated.

3. The apparatus of claim 2, further comprising:
a pair of redundant conductors electrically coupling the second electrode to the detection circuit; and
the detection circuit is further configured to test electrical continuity through the pair of redundant conductors.

4. The apparatus of claim 2, wherein the needle further comprises:
- a conductive wall extending around the conduit from the proximal end of the needle to the piercing distal tip of the needle, the wall having an uninsulated portion extending proximally from the distal-most end to form the first electrode;
- at least one nonconductive layer overlaying the conductive wall, the second and third electrodes being formed on the at least one nonconductive layer;
- a first conductive trace formed on the at least one nonconductive layer, the first conductive trace coupling the second electrode to the detection circuit;
- a second conductive trace formed on the at least one nonconductive layer and being electrically isolated from the first conductive trace, the second conductive trace coupling the third electrode to the detection circuit; and
- an outer insulation layer overlaying the first and second conductive traces.

5. The apparatus of claim 2, wherein the second electrode of the needle comprises a pair of redundant second electrodes; and the needle further comprises:
- a conductive wall extending around the conduit from the proximal end of the needle to the piercing distal tip of the needle, the wall having an uninsulated portion extending proximally from the distal-most end to form the first electrode;
- at least one nonconductive layer overlaying the conductive wall, the pair of second redundant electrodes and the third electrode being formed on the at least one nonconductive layer;
- a first conductive trace formed on the at least one nonconductive layer, the first conductive trace coupling one of the pair of redundant second electrodes to the detection circuit;
- a second conductive trace formed on the at least one nonconductive layer, the second conductive trace coupling the other of the pair of redundant second electrodes to the detection circuit;
- a third conductive trace formed on the at least one nonconductive layer and being electrically isolated from the first and second conductive traces, the third conductive trace coupling the third electrode to the detection circuit; and
- an outer insulation layer overlaying the first, second and third conductive traces.

6. The apparatus of claim 5, wherein each of the first and second conductive traces comprises a pair of redundant conductive traces; and the detection circuit is further configured to test electrical continuity through each pair of redundant conductive traces.

7. The apparatus of claim 2, wherein the needle further comprises:
- a conductive wall extending around the conduit from the proximal end of the needle to the piercing distal tip of the needle, the wall having an uninsulated portion extending proximally from the distal-most end to form the first electrode;
- a first conductive wire including insulated first and second segments that extend between the proximal end and the distal-most end of the needle, and an uninsulated third segment that extends between the first and second insulated segments to form the second electrode; and
- a second conductive wire including insulated first and second segments that extend between the proximal end and the distal-most end of the needle, and an uninsulated third segment that extends between the first and second insulated segments of the second wire to form the third electrode.

8. The apparatus of claim 2, further comprising:
- a power source;
- an electrical interconnect assembly configured to electrically couple the power source to the detection circuit;
- a housing containing the proximal end of the needle, the detection circuit, the power source, and the interconnect assembly; and
- a cap covering an opening into the housing, the cap having a hub in which a port is formed, the port being in fluid communication with the conduit of the needle, and the hub being configured for attachment to a syringe.

9. The apparatus of claim 8, wherein the cap is secured to the housing by one or more of: a snap-fit, a crush feature, adhesive bonding, and ultrasonic welding.

10. The apparatus of claim 8, wherein the confirmation signal and warning signal generated by the detection circuit each comprises a light signal, the confirmation signal being a different color light signal than the warning signal; and at least a portion of the cap is translucent to allow projection of the light signals therethrough.

11. The apparatus of claim 8, further comprising a needle guard, the needle guard including a shaft configured to contain the distal portion of the needle, and a battery tab protruding from a proximal end of the shaft; and wherein:
- the interconnect assembly includes a receptacle formed therein and a battery connector, the battery connector including a tab member located within the receptacle; and
- when the shaft of the needle guard is fitted around the distal portion of the needle, the battery tab of the needle guard extends into the receptacle of the housing and engages the tab member of the battery connector, the engagement preventing contact arms of the battery connector from making electrical contact with the detection circuit, and, when the fitted needle guard is removed from around the needle, the battery tab is pulled from the receptacle and disengages from the tab member, thereby allowing the contact arms to make electrical contact with the detection circuit.

12. The apparatus of claim 11, wherein the tab member of the battery connector includes an end configured to prevent reengagement of the battery tab of the needle guard after the needle guard has been removed from around the needle.

13. A transcutaneous filling apparatus for an implantable therapy delivery device, the apparatus comprising:
- a needle comprising a proximal end, a distal portion, a distal-most end, a piercing distal tip terminated by the distal-most end, a conduit extending along a length of the needle, from a proximal opening at the proximal end to a distal opening located in proximity to the distal-most end, a plurality of electrodes isolated from one another and spaced apart from one another along the distal portion of the needle; and
- a detection circuit electrically coupled to each electrode and configured to measure an impedance between each combination of pairs of the plurality of electrodes, to compare each measured impedance to a threshold impedance, and to generate a confirmation signal if at least one of the measured impedances is greater than the threshold impedance.

14. The apparatus of claim 13, wherein the plurality of electrodes comprises three electrodes; and the detection circuit generates a confirmation signal if two of the measured impedances is greater than the threshold impedance and the other of the measured impedances is less than the threshold impedance.

15. The apparatus of claim 14, wherein:
the therapy delivery device includes a fill chamber defined between a non-conductive septum of the device and a floor of the chamber, the septum having a first side and a second side defining a thickness thereof, the first side facing away from the chamber and the second side facing toward the floor of the chamber and being spaced apart from the floor by a distance; and
the second electrode includes a distal edge and a proximal edge, the proximal edge being spaced apart from the distal edge by a distance that is less than the thickness of the septum of the device, and the distal edge of the second electrode being spaced apart from the distal-most end of the needle by a distance that is greater than the distance by which the second side of the septum is spaced from the floor of the fill chamber of the device.

16. The apparatus of claim 13, wherein the therapy delivery device includes a fill chamber defined between a non-conductive septum of the device and a floor of the chamber, the septum having a first side and a second side defining a thickness thereof, the first side facing away from the chamber and the second side facing toward the floor of the chamber and being spaced apart from the floor by a distance; and wherein:
the needle further comprises a first insulative zone and a second insulative zone;
the plurality of electrodes of the needle comprise a first electrode located in proximity to the distal-most end, the first insulative zone extending proximally therefrom, a second electrode extending proximally from the first insulative zone, the second insulative zone extending proximally therefrom;
the second electrode includes a distal edge located adjacent the first insulative zone and a proximal edge located adjacent the second insulative zone, the proximal edge being spaced apart from the distal edge by a distance that is less than the thickness of the septum of the device, and the distal edge of the second electrode being spaced apart from the distal-most end of the needle by a distance that is greater than the distance by which the second side of the septum is spaced from the floor of the fill chamber of the device.

17. The apparatus of claim 13, further comprising:
a pair of redundant conductors electrically coupling a corresponding electrode to the detection circuit; and
the detection circuit is further configured to test electrical continuity through the pair of redundant conductors.

18. The apparatus of claim 13, wherein the needle further comprises:
a conductive wall extending around the conduit from the proximal end of the needle to the piercing distal tip of the needle, the wall having an uninsulated portion extending proximally from the distal-most end to form a first of the plurality of electrodes;
a nonconductive layer directly overlaying the inner wall;
a conductive layer deposited on the nonconductive layer, the conductive layer forming a second of the plurality of electrodes and a corresponding conductive trace that electrically couples the electrode to the detection circuit; and
an outer insulation layer overlaying the conductive trace.

19. The apparatus of claim 18, wherein the nonconductive layer overlaying the conductive wall is formed from a heat shrinkable material.

20. The apparatus of claim 13, further comprising:
a power source;
an electrical interconnect assembly configured to electrically couple the power source to the detection circuit;
a housing containing the proximal end of the needle, the detection circuit, the power source, and the interconnect assembly; and
a cap covering an opening into the housing, the cap having a hub in which a port is formed, the port being in fluid communication with the conduit of the needle, and the hub being configured for attachment to a syringe.

21. The apparatus of claim 20, wherein the signal generated by the detection circuit comprises a light signal; and at least a portion of the cap is translucent to allow projection of the light signal therethrough.

22. The apparatus of claim 20, wherein the cap is secured to the housing by one or more of: a snap-fit, a crush feature, adhesive bonding, and ultrasonic welding.

23. The apparatus of claim 20, further comprising a needle guard, the needle guard including a shaft configured to contain the distal portion of the needle, and a battery tab protruding from a proximal end of the shaft; and wherein:
the interconnect assembly includes a receptacle formed therein and a battery connector, the battery connector including a tab member located within the receptacle; and
when the shaft of the needle guard is fitted around the distal portion of the needle, the battery tab of the needle guard extends into the receptacle of the housing and engages the tab member of the battery connector, the engagement preventing contact arms of the battery connector from making electrical contact with the detection circuit, and, when the fitted needle guard is removed from around the needle, the battery tab is pulled from the receptacle and disengages from the tab member, thereby allowing the contact arms to make electrical contact with the detection circuit.

24. The apparatus of claim 23, wherein the tab member of the battery connector includes an end configured to prevent reengagement of the battery tab of the needle guard after the needle guard has been removed from around the needle.

* * * * *